US00PP35524P2

(12) United States Plant Patent
Hansen

(10) Patent No.: US PP35,524 P2
(45) Date of Patent: Dec. 5, 2023

(54) ***HOSTA* PLANT NAMED 'MY FAIR LADY'**

(50) Latin Name: ***Hosta* hybrid (Tratt.)**
Varietal Denomination: My Fair Lady

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 133 days.

(21) Appl. No.: 17/803,730

(22) Filed: Nov. 1, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02
See application file for complete search history.

*Primary Examiner* — Kent L Bell

(57) ABSTRACT

A new and distinct *Hosta* plant named 'My Fair Lady' producing medium-sized broadly horizontal mounds of basal, ovate to broadly ovate leaves with acute apices, cordate bases and flat margins. The leaves are variegated having dark green margins and creamy-yellow centers with intermediate color separation between the margin and center of variably large segments of several shades of chartreuse. The campanulate flowers beginning in mid-July are very pale lavender with white edges appearing on glaucous, light-green scapes. 'My Fair Lady' is useful in the landscape, as a container plant, a specimen or en masse.

2 Drawing Sheets

Botanical classification: *Hosta* hybrid (Tratt.).
Variety denomination: 'My Fair Lady'.

STATEMENT REGARDING PRIOR DISCLOSURES UNDER 37 CFR 1.77(B)(6)

*Hosta* 'My Fair Lady' was first introduced by the inventor as a non-enabling description in registration of the name in early 2021 with the International Cultivar Registration Authority for the genus *Hosta*. No plants of *Hosta* 'My Fair Lady' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'My Fair Lady' hereinafter also referred to as the new plant or by the cultivar name, 'My Fair Lady'. *Hosta* 'My Fair Lady' was hybridized by the inventor on Jul. 27, 2011, at a wholesale perennial nursery in Zeeland, Michigan, USA. The female parent was the proprietary unreleased hybrid known only by the hybrid number WGI-36 (not patented) and the male parent was 'Elatior' (not patented). The seeds from this cross were planted in late fall of 2011 and a single seedling selection from this cross eventually produced the new plant. The new plant was assigned the breeder code 11-338-4 and passed the initial evaluation in the summer of 2015. 'My Fair Lady' has been asexually propagated by division at the same nursery since 2018 and also by careful shoot tip plant tissue culture with the resultant asexually propagated plants having retained all the same traits as the original plant. *Hosta* 'My Fair Lady' has been stable and reproduced true to type plants in successive generations of asexual reproduction.

There are over 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant with green margins and variegated with creamy centers are: 'Angel Falls' U.S. Plant Pat. No. 28,785, 'American Sweetheart' (not patented), 'Sea Thunder' (not patented), 'Lakeside Paisley Print' (not patented), 'Cool As a Cucumber' (not patented), 'Lakeside Love Affaire' (not patented), 'Half and Half' (not patented), 'Miss America' U.S. Plant Pat. No. 32,068, 'Viva Las Vegas' (not patented) and 'Love Story' U.S. Plant Pat. No. 34,224.

The female parent has a smaller habit and smaller foliage size, the streaked foliar variegation is thinly spread out in sectors throughout the heavily-glaucous blue leaves. The male parent, 'Elatior', has a larger habit with larger and solid-green foliage, and the stapes are longer and more arching with larger and more numerous flowers.

The habit of 'Angel Falls' is slightly taller and more arching in habit with a more greenish-yellow leaf center earlier in the season, slightly more vein pairs at maturity, and the leaf apices are less acute. 'American Sweetheart' has thicker and stiffer foliage and more upright habit, and the leaves have a wider margin and narrower center with less intermediate variegated colors between the margin and center and the flower scapes are taller with larger flowers. 'Sea Thunder' has a smaller habit and smaller foliage with less intermediate colors between the margin and center. 'Lakeside Paisley Print' has stiffer and thicker-substance foliage with broader margins and narrower center variegation, the stapes become more lavender blushed, and the flowers are darker purple. 'Cool As a Cucumber' has longer more lanceolate and arching foliage. 'Lakeside Love Affaire' has a slightly smaller habit and foliage that is more broadly ovate with less intermediate colors between the margin and center variegation. 'Half and Half' has a shorter habit with smaller, thicker foliage with a heavier substance, and a narrower white center. 'Miss America' has a larger habit, stiffer and thicker foliage with broader margins and narrower variegated leaf center, and the flowers are larger, open wider, have a darker lavender center stripe and the scapes are erect, much taller with more numerous flowers. 'Viva Las Vegas' has foliage that is broader, more cordate and more bullate, and less sinuate and the margin color is more bluish-green. 'Love Story' has slightly larger foliage with longer and narrower apices and a more sinuate margin.

Other *Hosta* cultivars may have individual traits similar to 'My Fair Lady' but the new plant differs from the above-listed cultivars and all other *Hostas* known to the applicant, by the combination of the following traits:

1. Habit is a broadly horizontal mound;
2. Leaves are medium-sized, ovate to broadly ovate, with cordate bases;
3. Leaves are smooth with a flat margin and have slightly impressed adaxial veins;
4. Leaf margins are dark green with a creamy yellow center and intermediate color separation between the margin and center of variably large segments of several shades of chartreuse;
5. Campanulate flowers are very pale lavender beginning in mid-July on upright, light-green, glaucous scapes;
6. Flowers are moderately loosely arranged on stapes with the first flowers beginning to open well above the foliage;

BRIEF DESCRIPTION OF THE DRAWING

The photographs of the new plant demonstrate the overall appearance of the new plant, including the unique traits. The colors are as accurate as reasonably possible with color reproductions. Ambient light spectrum, temperature, source, and direction may cause the appearance of minor variation in color.

The drawings show a five-year-old 'My Fair Lady' plant in a trial garden at a nursery in Zeeland, MI with supplement fertilizer and water as needed.

DETAILED BOTANICAL DESCRIPTION

Figure 1:
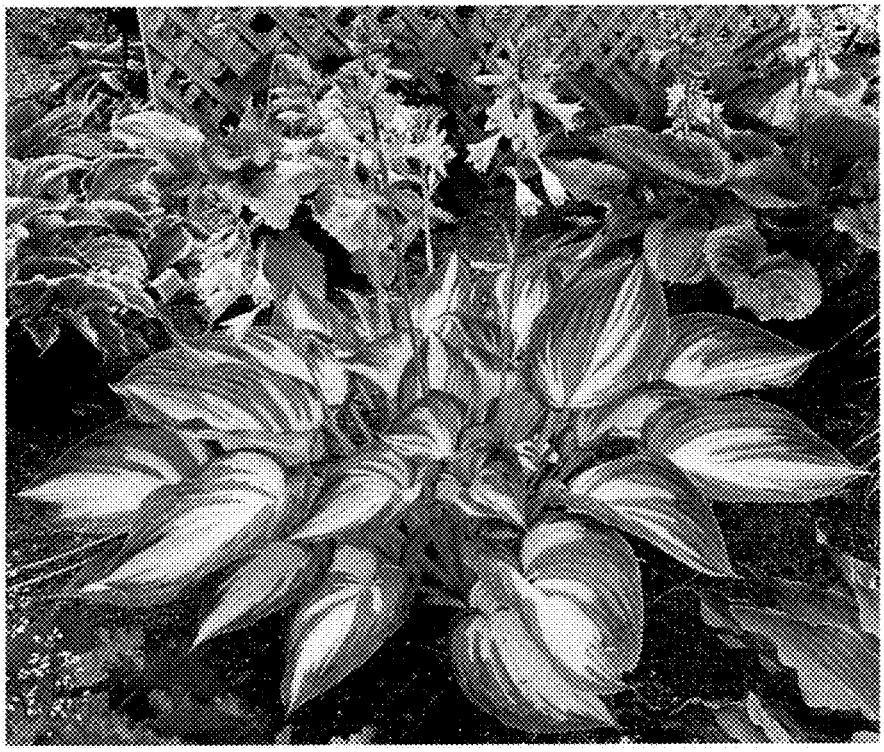
FIG. 1 shows the landscape foliage habit of a new plant prior to flowering.
Figure 2:
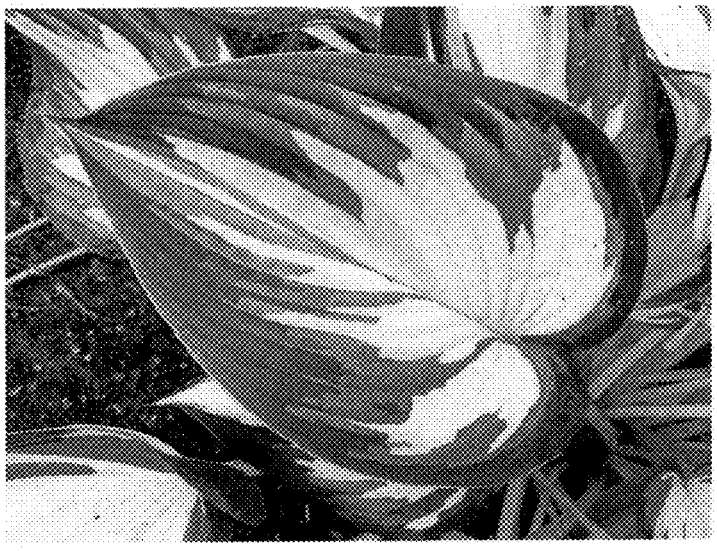
FIG. 2 shows a close-up of a leaf.
Figure 3:
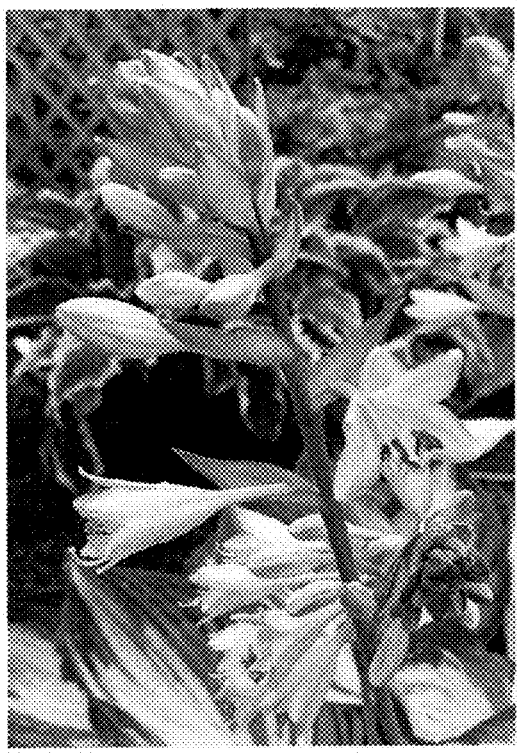
FIG. 3 shows a close-up of the flower, buds, and foliar bracts.

The following descriptions and color references are based on the 2015 edition of The Royal Horticultural Society Colour Chart except where common dictionary terms are used. The new plant, *Hosta* 'My Fair Lady', has not been observed under all possible environments. Those skilled in the art will appreciate that certain characteristics will vary with plants that are more mature or plants that are less mature. The phenotype may vary slightly with different environmental conditions, such as temperature, light, fertility, moisture, and maturity levels, but without any change in the genotype. The following observations and size descriptions are of a five-year-old plant in a shaded trial garden in Zeeland, Michigan with supplemental water and fertilizer.

Botanical classification: *Hosta* x hybrid;

Parentage: Female or seed parent is a proprietary hybrid WGI-36; male or pollen parent is 'Elatior';

Propagation: Garden division and sterile shoot tip tissue culture;

Time to initiate roots from tissue culture: About three weeks;

Growth rate: Moderately vigorous to slow;

Crop time: About four months to six months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a low medium-sized mound of outwardly extending petioles and leaves and arching scapes flowering above foliage;

Plant size: Foliage height to about 43.2 cm above soil line to the top or the leaves, to about 65 cm tall to the top of the flowers and to about 96.5 cm wide at the widest point just above the soil line;

Foliage description: Ovate to broadly ovate; narrowly acute apex, cordate base; margin entire; flat, not folded; and not bullate between the veins; glabrous and smooth both surfaces; adaxial slightly glaucous becoming matte, abaxial glaucous becoming lustrous; flexible; variegated;

Leaf blade size: To about 24 cm long and about 16 cm wide about one-third way from the base; average about 21 cm long and 14.5 cm wide;

Leaf blade color: Early season and expanding adaxial margin nearest RHS 137B, adaxial center nearest RHS 146C with intermediate zone nearest RHS 146B; early season and expanding abaxial margin nearest RHS 138B, abaxial center nearest RHS 148C without distinguishing intermediate zone colors; mid-season and mature adaxial margin between RHS 137A and RHS 137B, center between RHS 11C and RHS 11D and RHS 150D, with intermediate zone comprising colors of nearest RHS 146D, RHS 146B, and between RHS 146D and RHS 145A; abaxial mid-season and mature margin nearest RHS 137B, center nearest RHS 11D in high light and nearest RHS 4C in more shade, with intermediate zone comprising colors of nearest RHS 145A, RHS 148C, RHS 146D, and RHS 144A;

Veins: 11 to 12 pairs with midrib; slightly impressed adaxial and costate and smooth abaxial;

Vein color: Young veins in adaxial margin and center region nearest RHS 138B, young abaxial midrib nearest RHS 145D with primary veins nearest RHS 148C; mature veins in adaxial margin nearest RHS 146D and center nearest RHS 194B, mature abaxial, margin nearest RHS 146D and center nearest RHS NN155A;

Petiole: Glabrous and matte both adaxial and abaxial; moderately concavo-convex; stiff; to 28 cm long and 12 mm wide at base and about 4 mm deep, average about 23 cm long and 10 mm wide and 3 mm deep;

Petiole color: Young expanding foliage adaxial margin between RHS 138B and RHS 138A, center between RHS 145A and RHS 146D, abaxial margin nearest RHS 138A and center between RHS 150D and RHS 145D; mature adaxial margin nearest RHS 137C and center nearest RHS 2D, abaxial margin nearest RHS 137C and center nearest RHS 2D with midrib nearest RHS 145D;

Flower description:

Buds one to two days prior to opening: Clavate with acute apex and narrow tube and rounded base; about 45 mm long and 12 mm in diameter at the widest portion in the bulb, tube to about 16 mm long and to about 3 mm diameter at base, gradually tapering from bulb; bulb about 29 mm long;

Bud color: Near white in the center a blend of RHS NN155C and RHS 85D, with apical 6 mm variable nearest RHS 85C and RHS 85D, basal tube nearest RHS 85D;

Flowers: Perfect; incomplete; campanulate; attitude outwardly to slightly downwardly; to 60 mm long to exserted pistil; corolla to 55 mm long and 38 mm wide at apex, fused in basal 35 mm, free in the distal 20 mm, decreasing in size distally; corolla tube portion 18 mm long and gradually tapering to 3 mm diameter at base; with rounded base; flowers moderately loosely arranged on scape;

Flower aspect: Outwardly;

Flowering lasting: Persists for a normal period, usually about one day on the plant;

Flowering period: Scapes remain effective with flowers beginning mid-July for about three weeks; with about 30 flowers per scape; mostly secund;

Fragrance: No detectable fragrance;

Tepals: Two sets of three; lanceolate; entire margins; acute apex; fused in basal 35 mm; glabrous adaxial and abaxial; outer set reflexed, to about 11 mm wide near fusion and 55 mm long; inner set to about 10 mm wide and 55 mm long;

Tepal color: Outer set adaxial nearest RHS 85D in 2.5 mm wide longitudinal center and nearest RHS NN155D along edges, abaxial lighter than RHS 85D in flared portion and nearest RHS NN155D along edge; inner set adaxial nearest RHS 85D in 6 mm wide longitudinal center and nearest RHS NN155D along edges, abaxial lighter than RHS 85D in flared portion and nearest RHS NN155D along edge, with a transparent 0.5 mm wide margin; corolla tube adaxial nearest RHS NN155C, abaxial nearest RHS 85D;

Gynoecium: Single; to about 64 mm long; superior;

*Style*.—Cylindrical; glabrous; to about 58 mm long and 0.7 mm diameter; straight with distal 10 mm arcuate upwards 90°; color nearest RHS NN155A.

*Stigma*.—Puberulent; tri-lobed; about 1 mm long and 1 mm diameter; color nearest RHS NN155A.

*Ovary*.—Ellipsoidal: superior; apex rounded; base rounded to truncate; sides slightly furrowed, about 5 mm long and 2.5 mm diameter; color nearest RHS 145C.

Androecium: Six;

*Filaments*.—Six; cylindrical; approximately 57 mm long and 0.5 mm in diameter; curved or bent upwardly about 90° in the distal 8 mm; color nearest RHS NN155A.

*Anthers*.—Oblong with rounded ends; basifixed, longitudinally dehiscent; about 5 mm long and 2 mm wide and 1.5 mm thick when fully developed; color adaxial between RHS 65B and RHS 65C, abaxial nearest RHS 162C.

*Pollen*.—Abundant; spherical; less than 0.1 mm long; color nearest RHS 17A.

Peduncle: Cylindrical; usually one per mature division; about 5 per plant; glabrous; moderately glaucous: erect to slightly drooping distally; to about 65 cm in length and about 5 mm in diameter at base, average about 62 cm in length and 4 mm diameter at base;

Peduncle color: Between RHS 148C and RHS 138B without noticeable anthocyanin blush pigmentation;

Inflorescence: Flowering portion about 28 cm long and 7.5 cm wide; with faintly variegated bracts subtending each flower;

Pedicel: Cylindrical; glabrous; slightly lustrous; to about 20 mm long and 2.0 mm diameter, decreasing distally; attitude. arcuate outwardly;

Pedicel color: Nearest RHS 148D proximally and RHS 157D distally without significant anthocyanin;

Floral bracts: Each flower normally subtended by a single faintly variegated bract; lanceolate; narrowly acute apex and truncate base; entire margin; glabrous and slightly glaucous abaxial and adaxial; to about 38 mm long and 14 mm wide, decreasing distally; variegated margin about 1 mm wide;

Bract color: Proximal bracts at flowering adaxial and abaxial margin nearest RHS NN155B, adaxial and abaxial center between RHS 145A and RHS 146D; distal bracts at flowering adaxial margin between RHS N75D and RHS N77C, abaxial margin nearest RHS N77C, adaxial center nearest 145D and abaxial center between RHS 145D and RHS 146D;

Fruit: Non-fleshy, dehiscent, tri-loculicidal capsule; oblong ellipsoidal; attenuate base; rounded to apiculate apex; about 40 mm long and 7 mm in diameter; color as maturing variable, nearest RHS 155D with faint blushing nearest RHS N187B concentrated at sutures and sometimes in between sutures extending from base to about halfway to apex a longitudinal band between RHS 138A and RHS 143A, when nearly mature and prior to dehiscence nearest RHS 150D and upon dehiscence nearest RHS 161C;

Seeds: Elliptic; with flattened wing surrounding embryo positioned toward one end of ellipse; about 12 mm long, 3.5 mm wide, and 1.0 mm thick at embryo; up to 30 seeds per capsule; color nearest RHS N199A with maturity;

Pest and disease resistance: No observed resistance to slug feeding. Other resistance to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature.

Hardiness: At least from USDA zone 3 through 8, and other disease resistance is typical of that of other *Hostas*.

It is claimed:

1. A new and distinct *Hosta* plant named 'My Fair Lady' as herein described and illustrated.

* * * * *